United States Patent [19]

Cross

[11] 4,126,444
[45] Nov. 21, 1978

[54] SUBSTITUTED IMIDAZO (1,5-d)-AS-TRIAZIN-4-OLS, AND HERBICIDAL USE THEREOF

[75] Inventor: Barrington Cross, Rocky Hill, N.J.

[73] Assignee: American Cynamid Company, Stamford, Conn.

[21] Appl. No.: 853,977

[22] Filed: Nov. 22, 1977

[51] Int. Cl.$^2$ ............... C07D 285/20; C07D 403/04; A01N 9/22
[52] U.S. Cl. ........................................ 71/93; 544/184
[58] Field of Search ........................... 544/184; 71/93

[56] References Cited

U.S. PATENT DOCUMENTS 3,941,785  3/1976  Clarke et al. .................. 544/184

Primary Examiner—John M. Ford
Attorney, Agent, or Firm—Harry H. Kline

[57] ABSTRACT

There are provided substituted imidazo[1,5-d]-as-triazin-4-ols, useful as herbicides for the pre- and postemergence control of undesired mono- and dicotyledonous plants.

14 Claims, No Drawings

SUBSTITUTED IMIDAZO (1,5-d)-AS-TRIAZIN-4-OLS, AND HERBICIDAL USE THEREOF

SUMMARY OF THE INVENTION

The present invention relates to substituted imidazo[1,5-d]-as-triazin-4-ols which can be represented by formula (I) as follows:

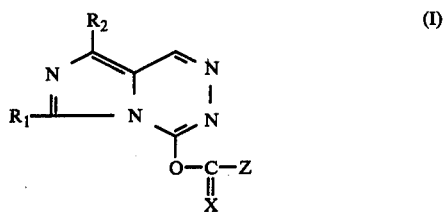

wherein $R_1$ is selected from the group consisting of alkyl $C_2$-$C_6$, cycloalkyl $C_3$-$C_6$ and phenyl which phenyl may be optionally monosubstituted with a substituent selected from alkyl $C_1$-$C_4$, alkoxy $C_1$-$C_3$, halo and $(CH_3)_2N-$; $R_2$ is selected from the group consisting of hydrogen, alkyl $C_1$-$C_3$ and halo; X is oxygen or sulfur; Z is selected from the group consisting of alkyl $C_1$-$C_8$, benzyl, benzyl optionally substituted with methyl methoxy or halo, phenyl, and phenyl optionally substituted with methyl, methoxy or halo.

A preferred group of compounds represented by formula (I) above are those, wherein $R_1$ is selected from cyclohexyl, phenyl or m-tolyl; $R_2$ is selected from methyl, bromo or chloro; X is oxygen; Z is selected from methyl, propyl or phenyl.

The invention further relates to the use of the above defined compounds for the pre- and postemergence control of undesired monocotyledonous and dicotyledonous plants.

The compounds represented by formula (I) may be readily prepared according to the following reactions:

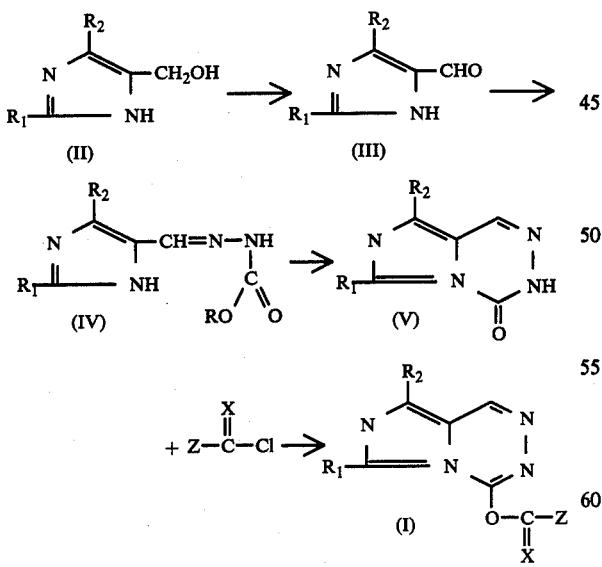

wherein R is alkyl $C_1$-$C_3$; and $R_1$, $R_2$, X and Z are as hereinabove defined.

In accordance with the above reactions, an appropriately substituted 4-imidazolemethanol (II) is oxidized with concentrated nitric acid to provide the corresponding 4-imidazolecarboxaldehyde (III). This oxidation may be carried out by suspending or dissolving each gram of starting material (II) in from about one ml. to about seven mls. of concentrated nitric acid and heating the reaction mixture at steam bath temperature for 2-3 hours. Alternatively, the reaction mixture may first be allowed to stand at room temperature for 8-16 hours and then heated for a short time (15-30 minutes) on the steam bath. The resulting reaction solution is preferably first diluted with water and then neutralized with any convenient base, such as caustic, soda ash, or concentrated aqueous ammonia. The precipitated product (III) is removed, washed with water, and purified by recrystallization from common organic solvents such as ethyl acetate, ethanol, and the like. Alternatively, the 4-imidazolemethanol (II) may be oxidized with activated manganese dioxide in chloroform, tetrahydrofuran, p-dioxane or t-butanol at the reflux temperature for a period of 4-6 hours to provide the 4-imidazolecarboxaldehyde (III).

The 4-imidazolecarboxaldehyde (III) may be readily converted to the 3-(4-imidazolylmethylene)carbazic acid ester (IV) by treatment with methyl, ethyl or propyl carbazate, respectively. This condensation is conveniently carried out in a lower alkanol or an aromatic hydrocarbon solvent, such as benzene or toluene, containing a small amount of glacial acetic acid at a temperature of 25°–120° C., whereupon the product (IV) forms and is removed by filtration. Cyclization of the 3-(4-imidazolylmethylene)carbazic acid ester (IV) is readily accomplished by heating in a non-polar high boiling solvent such as o-dichlorobenzene or diphenyl ether at 175°–275° C for 15–30 minutes or until the cyclization is essentially complete, whereby the corresponding imidazo[1,5-d]-as-trazin-4(3H)-ones (V) are obtained. Reacting the imidazo-as-triazin-ones (V) with an acid halide of formula:

wherein Z and X are as hereinabove defined and halogen may be chlorine or bromine, in pyridine or in an inert organic solvent in the presence of an acid acceptor leads to the desired formula (I) imidazo-as-triazin-4-ols.

The compounds (I) wherein $R_2$ is chloro or bromo, may be prepared by chlorination or bromination, respectively, of the corresponding imidazo[1,5-d]-as-triazin-4(3H)-ones (V) in an inert solvent such as chloroform or carbon tetrachloride at steam bath temperature, or in glacial acetic acid. The compounds (I) wherein $R_2$ is iodo may be prepared as follows:

The aldehyde (III) wherein $R_2$ is hydrogen is converted to the dimethyl acetal in methanol/HCl. The dimethyl acetal is iodinated in aqueous methanol in the presence of a base, and then hydrolyzed to yield the corresponding iodoaldehyde (IIIa).

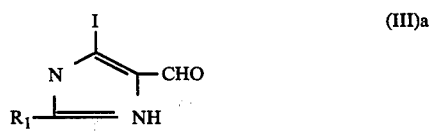

The thus-obtained iodoaldehyde (IIIa) is then converted by the above hereinabove described process to the desired compounds (I) wherein $R_2$ is iodo. It is to be noted that the last step of the latter procedure, namely, the reaction of the imidazo[1,5-d]-as-triazin-4(3H)-ones (V) with an acid halide of formula:

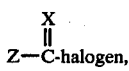
Z—C-halogen, may lead either to the N- or O- substitution as illustrated below:

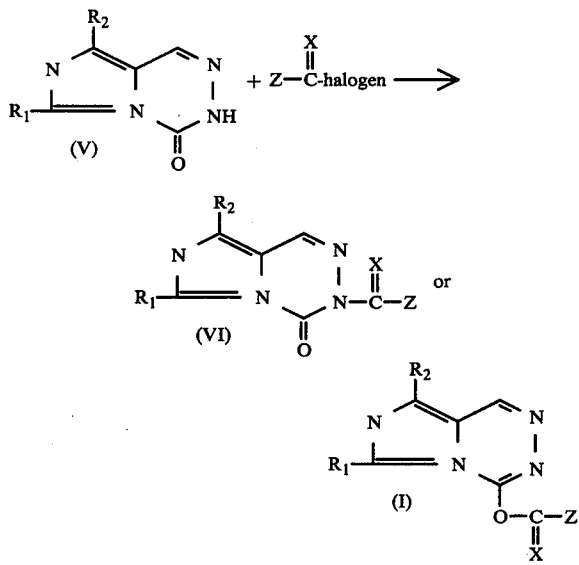

Available spectral data, however, favors O- substitution, namely, the compounds of formula (I).

It is further to be noted that, after application, both compounds of formulae (I) and (VI) may exist simultaneously, in equilibrium with each other, in the environment as shown below:

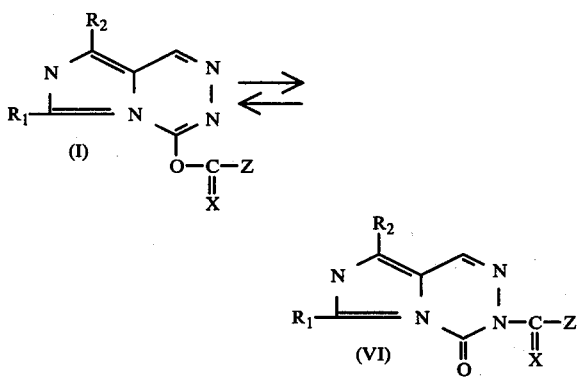

wherein said equilibrium may shift to favor one or the other of the above structures depending on the local conditions acting upon said equilibrium.

In accordance with the process of this invention, the following compounds can be prepared:

8-n-propyl-6-(m-tolyl)imidazo[1,5-d]-as-triazin-4-ol, 4-O-p-chlorobenzoate;

8-Chloro-6-cyclohexylimidazo[1,5-d]-as-triazin-4-ol, 4-O-octanoate;

8-bromo-6-cyclopropylimidazo[1,5-d]-as-triazin-4-ol, 4-O-phenylacetate;

8-bromo-6-(m-chlorophenyl)imidazo[1,5-d]-as-triazin-4-ol, 4-O-butyrate;

8-ethyl-6-(m-dimethylaminophenyl)imidazo[1,5-d]-as-triazin-4-ol, 4-O-acetate;

8-iodo-6-(p-anisyl)imidazo[1,5-d]-as-triazin-4-ol, 4-O-propionate;

8-fluoro-6-(p-tert-butylphenyl)imidazo[1,5-d]-as-triazin-4ol, 4-O-hexoate;

8-methyl-6-propylimidazo[1,5-d]-as-triazin-4-ol, 4-O-p-toluate;

8-bromo-6-hexylimidazo[1,5-d]-as-triazin-4-ol, 4-O-acetate;

8-Chloro-6-cyclopentylimidazo[1,5-d]-as-triazin-4-ol, 4-O-thioacetate;

8bromo-6cyclopropylimidazo[1,5-d]-as-triazin-4-ol, 4-O-(m-methoxybenzoate);

8-methyl-6-phenylimidazo[1,5-d]-as-triazin-4-ol, 4-O-p-chlorophenylacetate.

As hereinabove stated, the compounds represented by formula (I) are useful herbicidal agents for the control of both monocotyledonous and dicotyledonous plants. They are highly effective for the preemergence control of said undesirable plants when applied at a rate of from about 0.28 kg per hectare to 11.2 kg per hectare to soil containing seeds, seedlings or propagating organs of said broadleaf weeds, or grass plants.

The compounds of formula (I) are also effective for the postemergence control of said undesirable plant species when applied at the rate of from about 0.28 kg per hectare to about 11.2 kg per hectare to the foliage of said plants.

The imidazo[1,5-d]-as-triazin-4-ols of formula (I) are generally formulated as wettable powders, aqueous concentrates, emulsifiable concentrates, or flowable (thixotropic) concentrates which are usually dispersed in water or other inexpensive liquid diluent for application as a liquid spray. The above compounds may also be prepared as granular formulations containing, generally, about 10% to 15%, by weight of toxicant.

Typically, a wettable powder can be prepared by grinding together about 25% to 80% by weight of a formula (I) compound, about 2% to 5%, by weight, of a surfactant such as sodium N-methyl-N-oleoyl taurate, alkyl phenoxy polyoxyethylene ethanol, or sodium alkyl naphthalene sulfonate, 5% to 10% by weight of a dispersing agent such as a highly purified sodium lignosulfonate and 25% to 63% by weight of a finely divided carrier such as kaolin, attapulgite, diatomaceous earth, or the like.

A typical formulation prepared in accordance with the above description is as follows:

50% by weight of 8-methyl-6-phenylimidazo[1,5-d]-as-triazin-4-ol, 4-O-acetate, 3% by weight of sodium N-methyl-N-oleoyl taurate, 10% by weight of sodium lignosulfonate, and 37% by weight of kaolin.

Flowable (thixotropic) concentrates can be prepared by grinding together 40% to 60% by weight of a formula (I) toxicant, 1% to 4% by weight of the sodium salt of condensed naphthalene sulfonic acids, 2% to 3% by weight of a gelling clay, 2% by weight of propylene glycol, and from 54% to 32% by weight of water.

A typical granular formulation can be prepared by dissolving or dispersing the active compound in a solvent and applying the toxicant to a sorptive or nonsorptive carrier such as attapulgite, corn cob grits, pumice, talk or the like.

The broad spectrum herbicidal activity of formula (I) compounds allows efficient control of undesired vegetation along highways, railroad lines, right-of-ways under power transmission lines and along pipelines and under bridge approaches and/or wherever high degree of control of undesired vegetation is required.

This invention is further illustrated by the following examples.

EXAMPLE 1

2-phenyl-4-imidazolemethanol

This product is prepared by the methods of Dziuron et al., Arch. Pharm., 306, 347 (1973) and 307, 46 (1974).

EXAMPLE 2

5-Methyl-2-phenyl-4-imidazolemethanol

Benzamidine hydrochloride (100 g) is dissolved in a minimum of water (350 ml) at room temperature. Freshly distilled 2,3-butanedione (67 g) is added giving a yellow solution. Adjusting the pH to 6–7 with 2N sodium hydroxide gives a solid which is allowed to stand at 0° C for 2 hours, collected, pressed dry and then washed with acetone (100 ml). This material is heated with stirring on a steam bath with concentrated hydrochloric acid (855 ml) and water (2437 ml) for 4 hours giving a solution. Cooling to room temperature overnight and then to 0° C produces a solid which is collected and air dried. This solid is dissolved in ethanol (350 ml), filtered and cooled producing a gel, which is taken up in 250 ml of 50°–60° C water, adjusted to pH 5.5 with concentrated sodium hydroxide and then to pH 7–8 with solid potassium bicarbonate. The mixture is cooled to 0° C and the product is collected, washed with water, and air dried. This product is recrystallized from methanol (1000 ml) giving the title product, m.p. 197°–199° C.

Alternatively, this product may be prepared by the method of Imbach et al., Bull. Soc. Chim. France, 1971, 1052.

EXAMPLE 3

2-Phenyl-4-imidazolecarboxaldehyde

A mixture of 2-phenyl-4-imidazolemethanol (17.4 g) and concentrated nitric acid (13.4 ml) is heated on a steam bath for 2.5hours. Three drops of fuming nitric acid are added to initiate the reaction. Next, the pH is adjusted to 8 with concentrated aqueous sodium carbonate and the mixture is cooled to 0° C overnight. The solid is recovered, washed with water and recrystallized from a mixture of 70 ml of ethyl acetate and 20 ml of petroleum ether giving a yellow solid. Treatment of the mother liquor with petroleum ether gives an additional tacky substance which is triturated with 2-propanol giving a second solid. These two solids are taken up in hot 2-propanol and recrystallized as a yellow solid. This solid is recrystallized from ethanol:water (1:1) yielding yellow crystals, m.p. 169°–171.5° C.

EXAMPLE 4

5-Methyl-2-phenyl-4-imidazolecarboxaldehyde

5-Methyl-2-phenyl-4-imidazolemethanol (102.1 g) is dissolved in concentrated nitric acid (765 ml). The solution is cooled in an ice bath and allowed to stand for 16 hours. The solution is heated on a steam bath for 30 minutes, diluted with water (2.3 liters) and neutralized with 50% sodium hydroxide while cooling in an ice bath. The solid is collected, dried, recrystallized from ethanol (200 ml) and then from 1:2 ethanol:water (1000 ml) giving the title product, m.p. 102°–115° C.

Alternatively, this product may be prepared by the method of Diels et al., Chem. Ber. 49 1711 (1916).

EXAMPLE 5

3-[(5-methyl-2-phenyl-4-imidazolyl)methylene]carbazic acid ethyl ester

A mixture of 5-methyl-2-phenyl-4imidazolecarboxaldehyde (10.25 g), ethyl carbazate (5.72 g) and ethanol (30 ml) containing 1 drop of acetic acid is heated at the boil for 30 minutes. The mixture is then concentrated under an air stream on a steam bath. Next, carbon tetrachloride (50 ml) is added and the mixture cooled at 0° C overnight. The solid is collected giving the title product, m.p. 209°–211° C.

EXAMPLE 6

3-[(2-phenyl-4-imidazolyl)methylene]carbazic acid ethyl ester

2-Penyl-4-imidazolecarboxaldehyde (8.16 g) is dissolved in hot ethanol (200 ml). A hot solution of ethyl carbazate (5.52 g) in ethanol (50 ml) is added. A precipitate forms immediately and the mixture is heated and stirred for about 10 minutes. The mixture is then cooled to 0° C and the precipitate collected by filtration to yield the title product, m.p. 196°–200° C.

EXAMPLE 7

6-Phenylimidazo[1,5-d]-as-triazin-4(3H)-one

A mixture of 3-[(2-phenyl-4-imidazolyl)methylene]carbazic acid ethyl ester (7.76 g) and diphenyl ester (50 ml) is heated with stirring at 255°–265° C until effervescence subsides. The mixture is cooled to room temperature, diluted with petroleum ether. The precipitated solid is collected by filtration and recrystallized from methanol to yield the desired product, m.p. 245°–248° C.

EXAMPLE 8

8-Methyl-6-phenylimidazo[1,5-d]-as-triazin-4(3H)-one

A mixture of 3-[(5-methyl-2-phenyl-4-imidazolyl)methylene]carbazic acid ethyl ester (8.33 g, 0.03 mole) and diphenyl ether (60 ml) is heated with stirring at 215°–230° C for 20 minutes. The reaction mixture is cooled and diluted with petroleum ether (340 ml). The precipitate is collected and recrystallized from benzene (350 ml) to yield the title product, m.p. 182°–184.5° C.

EXAMPLE 9

6-Phenylimidazo[1,5-d]-as-triazin-4-ol, 4-O-acetate

Acetyl chloride (1.42 ml; d = 1.105; 0.02 mole) is added dropwise with stirring to a mixture of 6-phenylimidazo[1,5-d]-as-triazin-4(3H)-one (4.24 g, 0.02 mole), pyridine (6.7 ml. 0.08 mole) and benzene (100 ml). The reaction mixture is stirred for 2 hours at room temperature and then one hour at reflux. The reaction mixture is poured into ice/water, acidified with hydrochloric acid and extracted with benzene. The benzene layer is separated, washed with water and evaporated to yield 1.116 g (22.8%) of title product. The product is recrystallized from 2-propanol to afford a straw colored solid, m.p. 194°–196° C.

Analysis calculated for $C_{13}H_{10}N_4O_2$: C, 61.41; H, 3.96; N, 22.04.

Found: C, 59.98; H, 4.38; N, 20.47.

NMR indicates Trace presence of water and 2-propanol in the product.

EXAMPLE 10

8-Methyl-6-phenylimidazo[1,5-d]-as-triazin-4-ol, 4-O-acetate

8-Methyl-6-phenylimidazo[1,5-d]-as-triazin-4(3H)-one is reacted with acetyl chloride by the process of Example 1 to afford the title product, m.p. 174.5°–175° C.

Analysis calculated for $C_{14}H_{12}N_4O_2$: C, 62.68; H, 4.51; N, 20.89.

Found: C, 62.35; H, 4.33; N, 20.93.

EXAMPLE 11

8-Methyl-6-phenylimidazo[1,5-d]-as-triazin-4-ol, 4-O-butyrate

8-Methyl-6-phenylimidazo[1,5-d]-as-triazin-4(3H)-one is reacted with butyryl chloride by the process of Example 1 to afford the title product, m.p. 101°–101.5° C.

Analysis calculated for $C_{16}H_{16}N_4O_2$: C, 64.85; H, 5.44; N, 18.80.

Found: C, 64.48; H, 5.48; N, 18.80.

EXAMPLE 12

8-Methyl-6-phenylimidazo[1,5-d]-as-triazin-4-ol, 4-O-benzoate

8-Methyl-6-phenylimidazo[1,5-d]-as-triazin-4(3H)-one is reacted with benzoyl chloride by the process of Example 1 to afford the title product, m.p. 165°–165.5° C.

Analysis calculated for: $C_{19}H_{14}N_4O$: C, 69.08; H, 4.27; N, 16.96.

Found: C, 69.04; H, 4.39; N, 16.96.

EXAMPLE 13

Preemergence Herbicidal Activity

The preemergence herbicidal activity of the compounds of the present invention is exemplified by the following tests in which the seeds or propagating organs of a variety of monocotyledonous and dicotyledonous plants are separately mixed with potting soil and planted on top of approximately 2.5 cm of soil in separate cups. After planting, the cups are sprayed with the selected aqueous acetone solution containing test compound is sufficient quantity to provide the equivalent of about 0.07 kg to 11.2 kg per hectare of test compound per cup. The treated cups are then placed on greenhouse benches, watered and cared for in accordance with conventional greenhouse procedures. Three to five weeks after treatment, the tests are terminated and each cup is examined and rated according to the rating system provided below. The data obtained are reported in Table I below.

| Rating System: | % Difference in Growth from the Check |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth; that is, a definite physiological malformation but with an over-ill effect less than a 5 on the rating scale. | |

*Based on visual determination of stand, size, vigor, chlorosis, growth malformation and over-all plant appearance.

Plant Abbreviations

SE - Sesbania (*Sesbania exaltata*)
LA - Lambsquarters (*Chenopodium album*)
MU - Mustard (*Brassica kaber*)
PI - Pigweed (*Amaranthus retroflexus*)
RW - Ragweed (*Ambrosia artemisiifolia*)
MG - Morningglory (*Ipomoea purpurea*)
BA - Barnyardgrass (*Echinochloa crusgalli*)
CR - Crabgrass (*Digitaria sanguinalis*)
FO - Green Foxtail (*Setaria viridis*)
WO - Wild Oats (*Avena fatua*)
TW - Teaweed (*Sida spinosa*)
VL - Velvetleaf (*Abutilon theophrasti*)
JW - Jimsonweed (*Datura stramonium L.*)

TABLE I

Evaluation of the Preemergence Herbicidal Activity, of Compounds of the Invention for the Control of undersired monocotyledonous and dicotyledonous plants.

| Compound | Rate: kg/ha | SE | LA | MU | PI | RW | MG | TW | VL | JW | BA | CR | FO | WO |
|---|---|---|---|---|---|---|---|---|---|---|---|---|---|---|
| | 11.2 | 9 | | 9 | 9 | 9 | 9 | 9 | 9 | | 9 | 9 | 9 | 9 |
| | 2.24 | | 9 | | 9 | 9 | 9 | 9 | 9 | 9 | 9 | 9 | 9 | 9 |
| 8-Methyl-6-phenylimidazo- | 1.12 | | 9 | | 9 | 9 | 9 | 9 | 9 | 9 | 9 | 9 | 9 | 9 |
| [1,5-d]-as-triazin-4-ol, | 0.56 | | 9 | | 9 | 9 | 9 | 9 | 9 | 9 | 9 | 9 | 9 | 9 |
| 4-O-acetate | 0.28 | | 9 | | 6 | 2 | 8 | 9 | 9 | 9 | 7 | 7 | 8 | 9 |
| | 0.28 | | 9 | | 6 | 2 | 8 | 9 | 9 | 9 | 7 | 7 | 8 | 9 |
| | 0.07 | | 0 | | 0 | 0 | 0 | 0 | 0 | 0 | 0 | 0 | 0 | 0 |
| | 11.2 | 9 | | 9 | 9 | 9 | 9 | 9 | 9 | | 9 | 9 | 9 | 9 |
| | 2.24 | | 9 | | 9 | 9 | 9 | 9 | 9 | 9 | 9 | 9 | 9 | 9 |
| 8-Methyl-6-phenylimidazo- | 1.12 | | 9 | | 9 | 9 | 9 | 9 | 9 | 9 | 9 | 9 | 9 | 9 |
| [5-d]-as-triazin-4-ol, | 0.56 | | 9 | | 9 | 9 | 9 | 9 | 9 | 9 | 9 | 9 | 9 | 9 |
| 4-O-butyrate | 0.28 | | 9 | | 5 | 0 | 8 | 8 | 9 | 9 | 9 | 7 | 7 | 9 |
| | 0.14 | | 2 | | 0 | 0 | 0 | 2 | 0 | 0 | 2 | 2 | 2 | 2 |
| | 0.07 | | 0 | | 0 | 0 | 0 | 0 | 0 | 0 | 0 | 0 | 0 | 1 |
| | 11.2 | 9 | | 9 | 9 | 9 | 9 | 9 | 9 | | 9 | 9 | 9 | 9 |
| | 2.24 | | 9 | | 9 | 9 | 9 | 9 | 9 | 9 | 9 | 9 | 9 | 9 |
| 8-Methyl-6-phenylimidazo- | 1.12 | | 9 | | 9 | 9 | 9 | 9 | 9 | 9 | 9 | 9 | 9 | 9 |
| [1,5-d]-as-triazin-4-ol, | 0.56 | | 9 | | 9 | 9 | 9 | 9 | 9 | 9 | 9 | 9 | 9 | 9 |
| 4-O-benzoate | 0.28 | | 8 | | 9 | 3 | 9 | 9 | 5 | 9 | 9 | 9 | 9 | 9 |
| | 0.14 | | 7 | | 0 | 3 | 0 | 3 | 0 | 9 | 3 | 6 | 2 | 7 |
| | 0.07 | | 0 | | 0 | 0 | 0 | 0 | 0 | 7 | 0 | 0 | 0 | 0 |
| | 11.2 | 9 | | 9 | 9 | 8 | 9 | 9 | 9 | | 9 | 9 | 9 | 9 |
| 6-phenylimidazo[1,5-d]-as- | 2.24 | | 8 | | 9 | 8 | 9 | 9 | 9 | 5 | 7 | 8 | 7 | 7 |
| triazin-4-ol, 4-O-acetate | 1.12 | | 6 | | 6 | 0 | 0 | 6 | 8 | 1 | 2 | 2 | 0 | 0 |
| | 0.56 | | 0 | | 3 | 0 | 0 | 0 | 0 | 0 | 0 | 0 | 0 | 0 |
| | 0.28 | | 0 | | 0 | 0 | 0 | 0 | 0 | 0 | 0 | 0 | 0 | 0 |

EXAMPLE 14

Postemergence Herbicidal Activity

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in separate cups for about 2 weeks. The test compounds are dispersed in 50/50 acetone/water mixtures containing 0.5% TWEEN® 20, a polyoxyethylene sorbitan monolaurate surfactant of Atlas Chemical Industries, in sufficient quantity to provide the equivalent of about 0.07 kg to 11.2 kg per hectare of active compound when applied to the plants through a spray nozzle operating at 2.81 kg/cm² pressure for a predetermined time. After spraying, the plants are placed on greenhouse benches and are cared for in the usual manner, commensurate with conventional greenhouse practices. Two weeks after treatment, the seedling plants are examined and rated according to the rating system set forth in Example 13. The data obtained are reported in Table II below.

TABLE II
Evaluation of the Postemergence Herbicidal Activity of Compounds of the Invention for the Control of Undesired Monocotyledonous and dicotyledonous plants.

| Compound | Rate: kg/ha | SE | LA | MU | PI | RW | MG | TW | VL | JW | BA | CR | FO | WO |
|---|---|---|---|---|---|---|---|---|---|---|---|---|---|---|
| | 11.2 | 9 | | 9 | 9 | 9 | 9 | 9 | 9 | | 9 | 9 | 9 | 9 |
| | 2.24 | | 9 | | 9 | 9 | 9 | 9 | 9 | 9 | 7 | 8 | 7 | 2 |
| 8-Methyl-6-phenylimidazo- | 1.12 | | 9 | | 9 | 0 | 9 | 7 | 8 | 9 | 3 | 7 | 2 | 1 |
| [1,5-d]-as-triazin-4-ol, | 0.56 | | 8 | | 9 | 0 | 9 | 6 | 7 | 9 | 1 | 1 | 1 | 1 |
| 4-O-acetate | 0.28 | | 3 | | 9 | 0 | 6 | 5 | 2 | 0 | 0 | 0 | 0 | 0 |
| | 0.14 | | 1 | | 7 | 0 | 8 | 0 | 0 | 0 | 0 | 0 | 0 | 0 |
| | 0.07 | | 0 | | 5 | 0 | 2 | 0 | 0 | 0 | 0 | 0 | 0 | 0 |
| | 11.2 | 9 | | 9 | 9 | 9 | 9 | 9 | 9 | | 9 | 9 | 9 | 9 |
| | 2.24 | | 9 | | 9 | 9 | 9 | 9 | 9 | 9 | 9 | 9 | 7 | 1 |
| 8-Methyl-6-phenylimidazo- | 1.12 | | 9 | | 9 | 6 | 9 | 9 | 9 | 9 | 8 | 9 | 3 | 1 |
| [1,5-d]-as-triazin-4-ol, | 0.56 | | 7 | | 9 | 3 | 9 | 1 | 9 | 1 | 5 | 7 | 1 | 0 |
| 4-O-butyrate | 0.28 | | 5 | | 9 | 0 | 6 | 0 | 1 | 1 | 0 | 0 | 0 | 0 |
| | 0.14 | | 0 | | 0 | 0 | 3 | 0 | 0 | 0 | 0 | 0 | 0 | 0 |
| | 0.07 | | 0 | | 0 | 0 | 1 | 0 | 0 | 0 | 0 | 0 | 0 | 0 |
| | 11.2 | 9 | | 9 | 9 | 9 | 9 | 9 | 9 | | 9 | 7 | 8 | 8 |
| | 2.24 | | 9 | | 9 | 9 | 9 | 9 | 9 | 9 | 9 | 9 | 9 | 1 |
| 8-Methyl-6-phenylimidazo- | 1.12 | | 9 | | 9 | 1 | 9 | 3 | 2 | 9 | 5 | 2 | 5 | 1 |
| [1,5-d]-as-triazin-4-ol, | 0.56 | | 8 | | 9 | 0 | 7 | 0 | 2 | 7 | 5 | 1 | 1 | 0 |
| 4-O-benzoate | 0.28 | | 2 | | 7 | 0 | 8 | 0 | 0 | 1 | 0 | 0 | 0 | 0 |
| | 0.14 | | 2 | | 3 | 0 | 2 | 0 | 0 | 1 | 0 | 0 | 0 | 0 |
| | 0.07 | | 0 | | 0 | 0 | 0 | 0 | 0 | 0 | 0 | 0 | 0 | 0 |

We claim:

1. A compound of the formula:

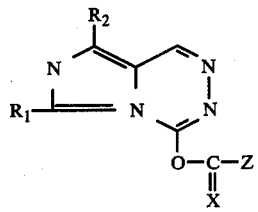

wherein $R_1$ is a member selected from the group consisting of alkyl $C_2$-$C_6$, cycloalkyl $C_3$-$C_6$, phenyl and mono-substituted phenyl, wherein said substituent is selected from alkyl $C_1$-$C_4$, alkoxy $C_1$-$C_3$, halo and $(CH_3)_2N-$; $R_2$ is a member selected from the group consisting of hydrogen, alkyl $C_1$-$C_3$ and halo; X is oxygen or sulfur; Z is a member selected from the group consisting of alkyl $C_1$-$C_8$, benzyl, mono-substituted benzyl, phenyl and mono-substituted phenyl wherein said substituents of said benzyl and phenyl moieties are selected from the group consisting of methyl, methoxy and halo.

2. A comound according to claim 1 wherein $R_1$ is selected from cyclohexyl, phenyl or m-tolyl; $R_2$ is selected from methyl, bromo or chloro; X is oxygen; Z is selected from the group consisting of methyl, propyl or phenyl.

3. A compound according to claim 1, 8-methyl-6-phenylimidazo[1,5-d]-as-triazin-4-ol, 4-O-acetate.

4. A compound according to claim 1, 8-methyl-6-phenylimidazo[1,5-d]-as-triazin-4-ol, 4-O-butyrate.

5. A compound according to claim 1, 8-methyl-6-phenylimidazo[1,5-d]-as-triazin-4-ol, 4-O-benzoate.

6. A compound according to claim 1, 6-phenylimidazo[1,5-d]-as-triazin-4-ol, 4-O-acetate.

7. A method for the pre- and postemergence control of undesired monocotyledonous and dicotyledonous plants comprising applying to the foliage of said plants or to the soil in which the seeds and other propagating organs of said plants germinate and grow a herbicidally effective amount of a compound of formula:

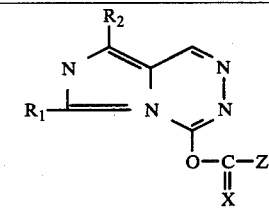

wherein $R_1$ is a member selected from the group consisting of alkyl $C_2$-$C_6$, cycloalkyl $C_3$-$C_6$, phenyl and mono-substituted phenyl wherein said substituent is selected from alkyl $C_1$-$C_4$, alkoxy $C_1$-$C_3$, halo and $(CH_3)_2N-$; $R_2$ is a member selected from the group consisting of hydrogen, alkyl $C_1$-$C_3$ and halo; X is oxygen or sulfur; Z is a member selected from the group consisting of alkyl $C_1$-$C_8$, benzyl mono-substituted benzyl, phenyl and mono-substituted phenyl wherein said substituents of said benzyl and phenyl moieties are selected from the group consisting of methyl, methoxy and halo.

8. A method according to claim 7, wherein $R_1$ is selected from cyclohexyl, phenyl or m-tolyl; $R_2$ is selected from methyl, bromo and chloro; X is oxygen, Z is selected from the group consisting of methyl, propyl and phenyl.

9. A method according to claim 7, wherein said compound is 8-methyl-6-phenylimidazo[1,5-d]-as-triazin-4-ol, 4-O-acetate.

10. A method according to claim 7, wherein said compound is 8-methyl-6-phenylimidazo[1,5-d]-as-triazin-4-ol, 4-O-butyrate.

11. The method according to claim 7, wherein said compound is 8-methyl-6-phenylimidazo[1,5-d]-as-triazin-4-ol, 4-benzoate.

12. The method according to claim 7, wherein said compound is 6-phenylimidazo[1,5-d]-as-triazin-4-ol, 4-O-acetate.

13. The method according to claim 7, wherein said compound is applied at a rate from 0.28 kg to 11.2 kg per hectare.

14. A method for preparing the compound of claim 1 which comprises: oxidizing a 4-imidazolemethanol having the formula:

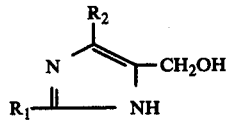

wherein $R_1$ is a member selected from the group consisting of alkyl $C_2$–$C_6$, cycloalkyl $C_3$–$C_6$, phenyl and mono-substituted phenyl wherein said substituent is selected from alkyl $C_1$–$C_4$, alkoxy $C_1$–$C_3$, halo and $(CH_3)_2N$—; $R_2$ is a member selected from the group consisting of hydrogen, alkyl $C_1$–$C_3$ and halo; subjecting resultant 4-imidazocarboxaldehyde to reaction with a carbazate selected from the group consisting of methyl carbagate, ethyl carbazate or propyl carbazate to recover a product having the formula:

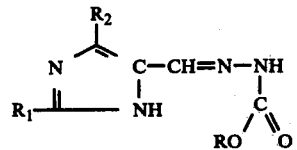

wherein R is alkyl $C_1$–$C_3$, and $R_1$ and $R_2$ are as above defined, cyclizing the latter product in the presence of an inert nonpolar solvent to obtain the corresponding imidazo[1,5-d]-as-triazin-4-(3H)-ones, subjecting the latter to the action of an acid halide having the formula:

wherein Z is alkyl ($C_1$–8) phenyl, benzyl or monosubstituted benzyl or phenyl, X is oxygen or sulfur, and thereafter recovering the desired product.

* * * * *